(12) United States Patent
Scrivens et al.

(10) Patent No.: US 6,867,049 B1
(45) Date of Patent: Mar. 15, 2005

(54) METHOD FOR OBTAINING INCREASED PARTICLE CONCENTRATION FOR OPTICAL EXAMINATION

(75) Inventors: Brian G. Scrivens, Colora, MD (US); Dwight Livingston, Fallston, MD (US); Robert S. Frank, Ellicott City, MD (US); Klaus W. Berndt, Timonium, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 402 days.

(21) Appl. No.: 09/670,739

(22) Filed: Sep. 27, 2000

(51) Int. Cl.⁷ .............................. B01L 3/00; G01N 1/40
(52) U.S. Cl. ...................... 436/177; 436/180; 422/68.1; 422/255; 422/58; 422/99; 422/228; 422/946; 422/947; 422/948; 422/100; 204/767; 137/544; 137/861; 137/883; 137/44
(58) Field of Search .................................. 436/177, 180; 422/68.1, 255, 58, 99, 228, 946, 947, 948, 100; 204/767; 137/544, 861, 883, 44

(56) References Cited

U.S. PATENT DOCUMENTS

| | | | | |
|---|---|---|---|---|
| 4,426,451 A | * | 1/1984 | Columbus | 436/518 |
| 4,618,476 A | * | 10/1986 | Columbus | 422/100 |
| 4,963,498 A | * | 10/1990 | Hillman et al. | 436/69 |
| 6,454,945 B1 | * | 9/2002 | Weigl et al. | 210/634 |
| 6,465,257 B1 | * | 10/2002 | Parce et al. | 436/180 |
| 6,599,480 B1 | * | 7/2003 | Scrivens et al. | 422/101 |

* cited by examiner

Primary Examiner—Monique T. Cole
(74) Attorney, Agent, or Firm—Bruce S. Weintraub

(57) ABSTRACT

The present invention relates to a method and apparatus for analyzing a blood or other biological fluid sample in a quiescent state, whereby particulate constituents of biological samples that contain sparse populations of interesting cellular species can be enumerated and inspected using an optical scanning instrument. Specifically, this invention relates to a method and apparatus for obtaining increased cellular or particulate concentrations within the use of said optical scanning method.

18 Claims, 5 Drawing Sheets

METHOD FOR OBTAINING INCREASED PARTICLE CONCENTRATION FOR OPTICAL EXAMINATION

FIELD OF THE INVENTION

The present invention relates to a method and apparatus for analyzing a blood or other biological fluid sample in a quiescent state, whereby particulate constituents of biological samples that contain sparse populations of cellular species of interest can be enumerated and inspected using an optical scanning instrument. Specifically, this invention relates to a method and apparatus for obtaining an increased cellular or particulate concentration within the use of said optical scanning method.

BACKGROUND OF THE INVENTION

The formation of appropriate cellular or particulate layers for later optical examination is important to many fields. One of these fields is hematology, where several methods and devices have been described for obtaining clinically useful cell concentrations.

A method and apparatus for analyzing a blood or other biologic fluid sample in a quiescent state without the need for separate fluid streams passing through the blood sample during the analysis is described in U.S. Ser. Nos. 09/248,135 and 09/249,721. Although this method simplifies the analysis procedure and yields the full compliment of CBC parameters it also possesses several disadvantages. One disadvantage of the apparatus is that the concentration of cells in the examination layer is not controlled. This can lead to difficulties in optically examining cell volume and morphology. Another disadvantage of the aforementioned apparatus is that the field of cells may be too sparse in clinically relevant samples to complete scanning in a timely manner.

U.S. Pat. Nos. 5,627,041 and 5,912,134 describe an apparatus and method for cytometric measurement of cell populations using fluorescent markers. However, a disadvantage of this method is that, if the sample under test is blood, it requires addition of diluent in such quantities that white blood cells (WBCs) with depressed counts are not very numerous in the sample and may require extremely long examination times to locate them. Moreover, if the cell counts within the undiluted blood are low, clinically relevant cell populations present in the sample may not be detected in the diluted sample. For example, patients who undergo chemotherapy regimens may have depressed white cell counts in the range of 1000 cells/$\mu$L and less. Cytometric examinations are typically searching for a sub-population of these cells, further reducing the likelihood of locating them.

U.S. Pat. No. 4,790,640 discloses a wedge shaped device for trapping rigid particles, such as sickle cells in blood. However, a disadvantage of the device is that the selection of cell sizes is accomplished by thickness of the chamber alone, which can exhibit substantial manufacturing variation over the examination area, causing a corresponding loss of ability to separate by size.

Consequently, it would be desirable to have a method and apparatus for obtaining the desired cellular concentration in a blood or other biologic sample which can mitigate the effect of a separate dilution step and addition of diluting fluids.

SUMMARY OF THE INVENTION

It is an objective of the present invention to provide channels in a separation wall inside a separation chamber, said channels having appropriate size and dimensions to allow at least one undesired particle species to pass while excluding larger particles from passing through, thereby arriving at a predetermined increased volume fraction of the desired particles.

It is another objective of the present invention to incorporate at least two separating channels in a separation wall in a separation chamber, the channels having channel sizes selected to allow at least one cell species and the substantially liquid component of the sample to pass through them, arriving at a desired concentration of larger cell types in the first compartment in front of the separation wall. A further embodiment of the present invention is to have a plurality of separating channels in the separating wall having one channel size selected to allow at least one cell species and the substantially liquid component of the sample to pass through them.

It is a further objective of the present invention to regulate the volume fraction of cellular or particle components of a specimen by means of an array of separating channels which effect their selection by means of size exclusion during flow between two adjoining compartments.

It is another objective of the present invention to increase the concentration of larger particles for cytometric examination of sparse populations by allowing only smaller particles and substantially liquid components to pass through the channels into a subsequent chamber.

It is a still further objective of the present invention to create an accurate spacing between two opposing containment walls to allow for the optimal formation of desired regions where all particles of interest lie in the same focal plane, allowing an accurate determination of the chamber thickness without relying on extraneous equipment and manipulations for height calibration.

DETAILED DESCRIPTION OF THE INVENTION

The present invention relates to a method and apparatus for obtaining an increased cellular or particulate concentration in a substantially dilute sample. The apparatus includes a sample chamber which has opposing sample containment walls, at least one of which is transparent. The sample chamber is separated into adjoining compartments which are in fluid communication by means of a multiplicity of channels aligned substantially parallel to each other and which traverse a separating wall between the two compartments. Filling of the chamber results in a substantially quiescent sample ready for further examination.

In a preferred embodiment, a chamber is used to manipulate blood components and one type of channel in the array is of sufficient size and dimensions to allow red blood cells (RBCs) to pass while excluding larger white blood cells (WBCs). The dimensions of the channel to create the desired size exclusion are nominally, in a preferred embodiment, 3 to 10 µm deep×5 to 50 µm wide. Dimensions within this range have been selected to effect the desired volume flow rate of RBCs, or particle-containing sample. In a modification of the invention, another type of channel in the array is of sufficient size and dimensions to exclude RBCs and WBCs from passing while allowing the liquid component of the specimen to pass freely. The dimensions of the channel to create the desired size exclusion are nominally, in a preferred embodiment, 0.5 to 1.5 µm deep×50 to 1000 µm wide. Dimensions within this range are selected to effect the desired volume flow rate of the liquid-only portion of the sample.

As the blood sample or particle containing specimen flows from the first compartment and through the array of channels into the subsequent compartment, the relative volume fraction of WBCs, RBCs, or other particles is increased in the first compartment. The two streams, one containing substantially undiluted blood or particles, and the other, a liquid-only fraction, recombine in the subsequent compartment to form a liquid sample having a reduced volume fraction of cells or particles in the subsequent compartment. A further benefit of the invention is to provide a thickness within the chamber during manufacture, which is more accurate than would otherwise be obtained since the wall surrounding the interior of the chamber acts to hold the two opposing sample containment walls, that function as optical windows apart at a fixed and accurate distance.

Figure 1:
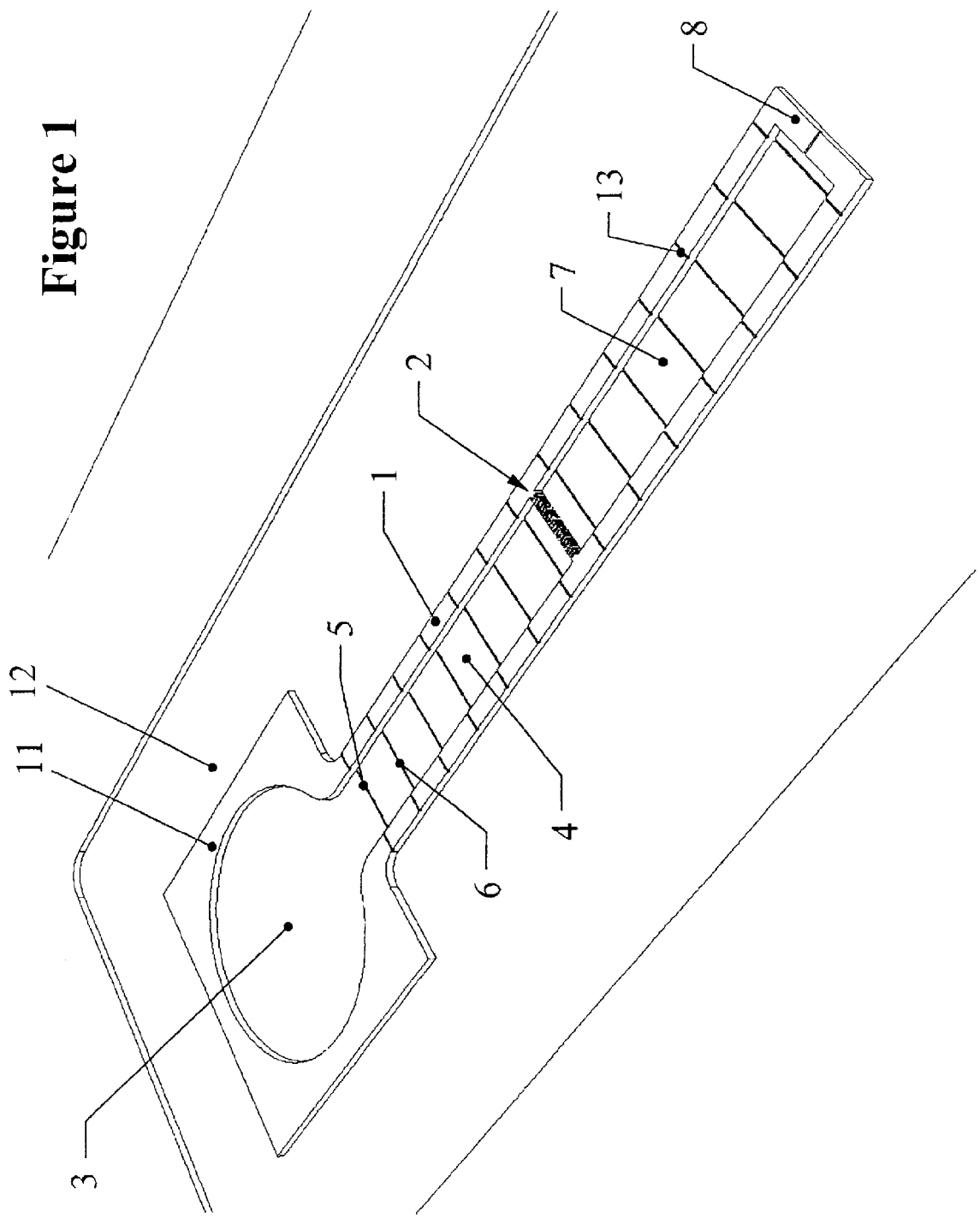
FIG. 1 is an isometric view of the particle separation chamber with the lid removed showing the separation channels and adjacent cell examination areas.

FIG. 1 is merely exemplary and is not intended to limit the present invention in any way. A separation chamber in accordance with the present invention can have notches in one or more compartments of the separation chamber, or no notches at all.

Figure 2:
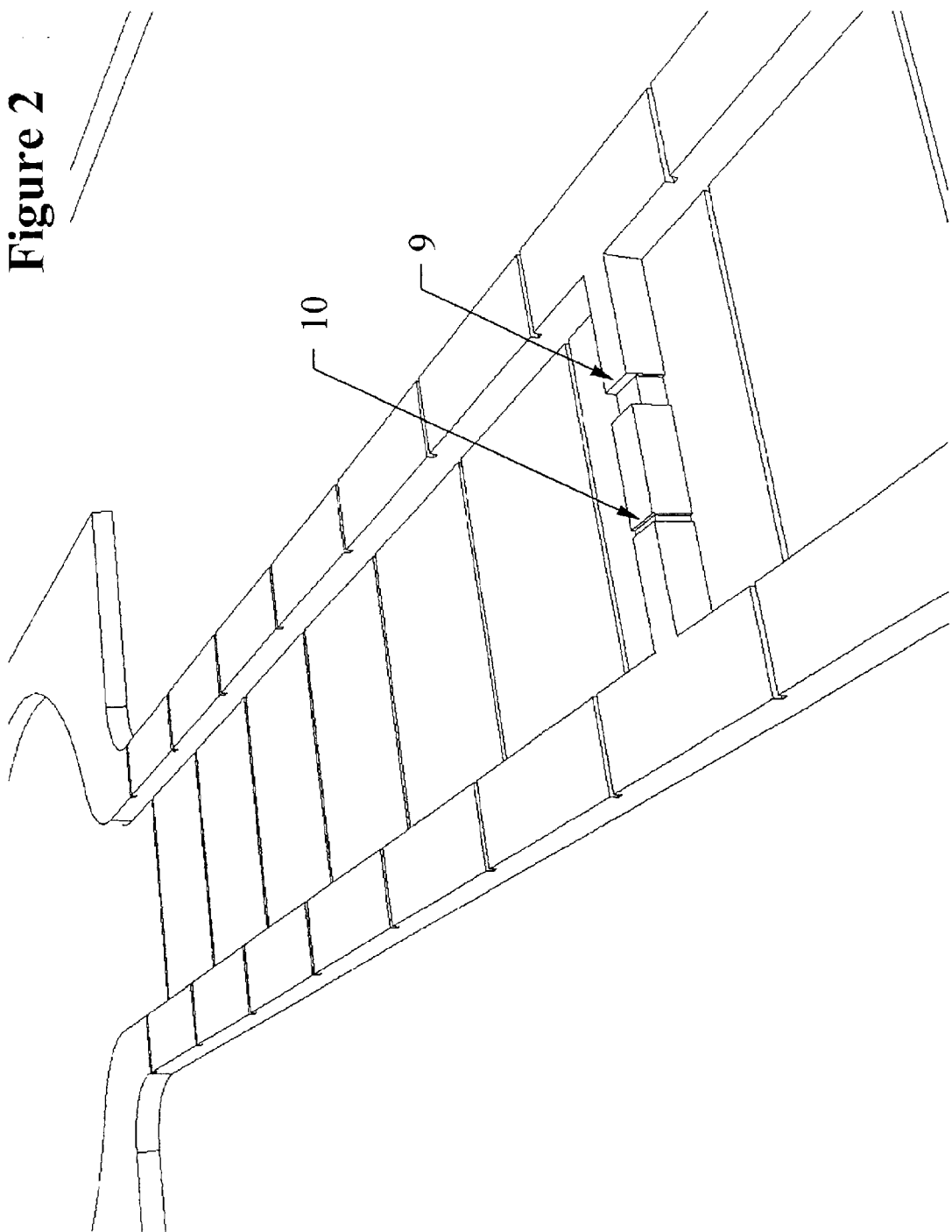
FIG. 2 is an isometric view of the bottom portion of the separation chamber showing the disposition of the separation channels.
Figure 3:
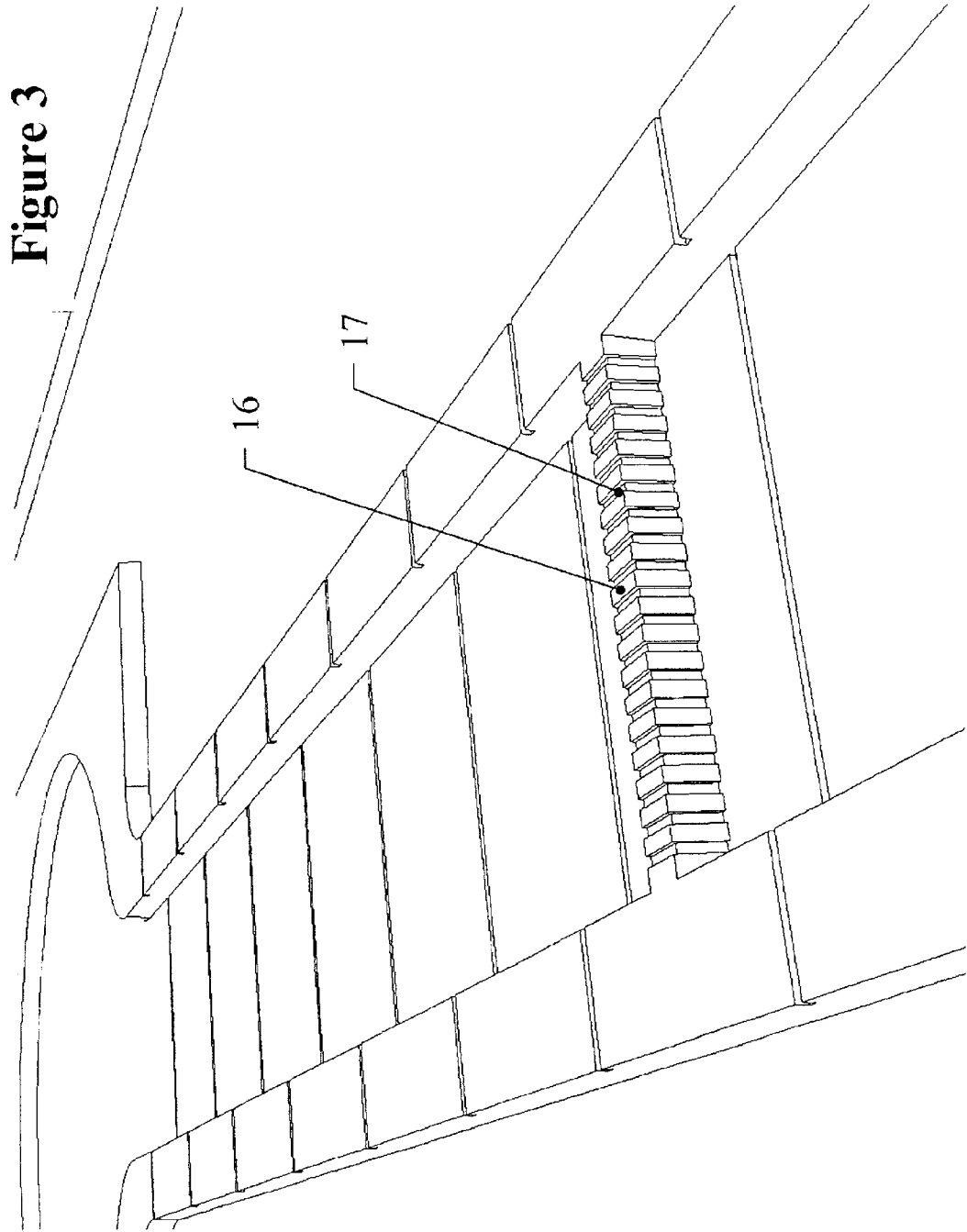
FIG. 3 shows a detailed view of another embodiment of the separation channels.
Figure 4:
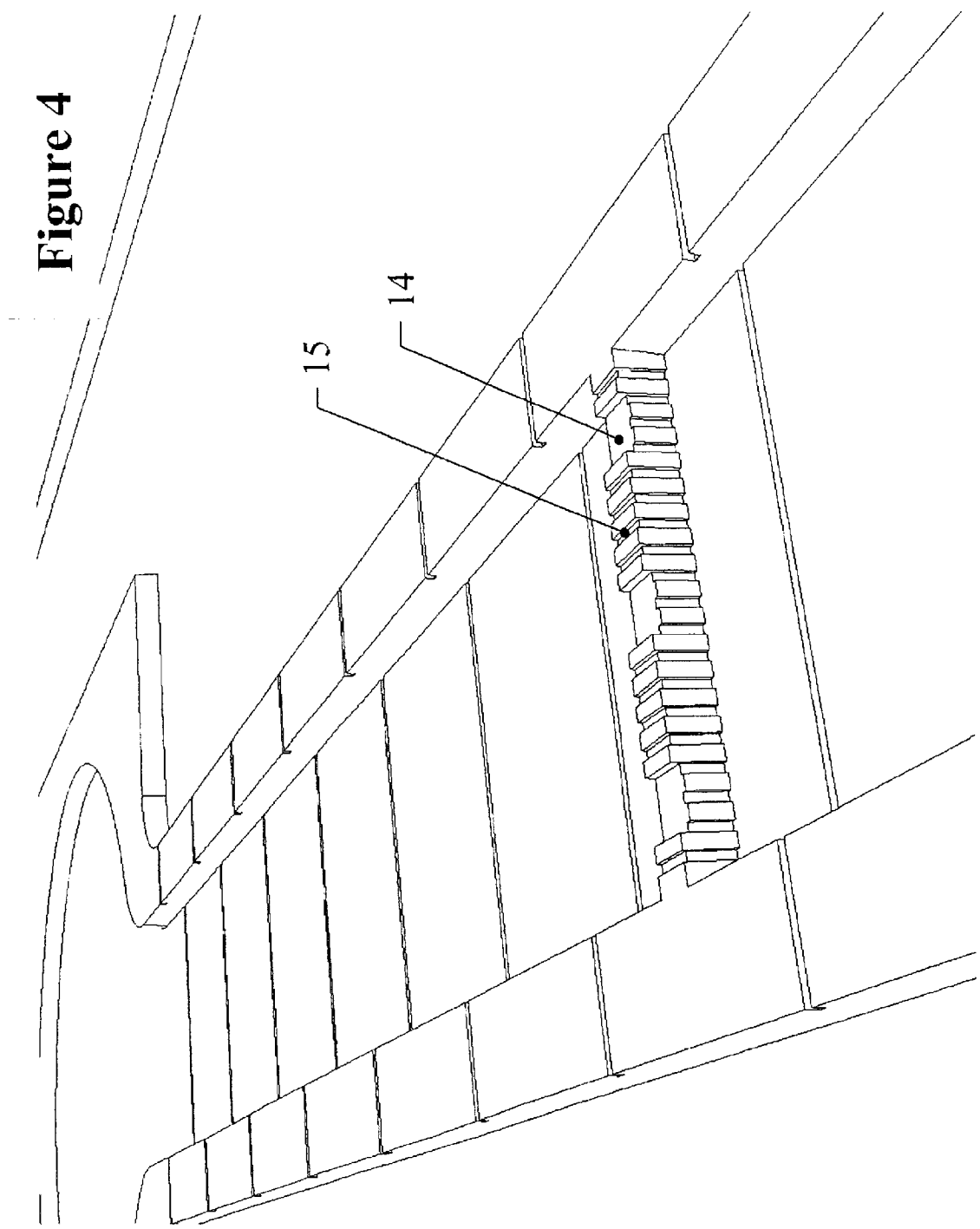
FIG. 4 shows an isometric view of another embodiment of the separation channels.

In the embodiment of the present invention demonstrated in FIG. 1, the separation chamber is surrounded by a wall (1) which is used to carry an, optically transparent lid (not shown) allowing for optical observation and to contain the liquid sample. The separation chamber is divided into two compartments by a separation wall (2) which has separation channels on top of it. Details of different embodiments for separation wall (2) are shown in FIGS. 2, 3, and 4. Returning to FIG. 1, fluid fills the first compartment through a sample entrance (3), which is surrounded by an extension (11) of wall (1), and moves into the first compartment (4) of the chamber. Upon proceeding, the liquid encounters a first notch (5) displaced laterally across the flow path. The notch creates a momentary barrier to progression of the advancing fluid meniscus until the meniscus has contacted the notch across the whole width of the chamber. Eventually the fluid wets into the notch, allowing the fluid to advance to the next notch (6) where the meniscus is again evened out. The fluid advance continues in this manner until it reaches the separation wall (2). The fluid continues to advance through the separation wall and separation channels to the second compartment (7) until finally stopping at its far end (8). Adequate venting of air while the chamber fills with liquid is provided by a series of venting-channels (13) on top of wall (1). To allow for a free passage of air out of channels (13), walls (1) and (11) are surrounded by a moat (12). During the filling process, the particles of interest, are prevented from passing through the separation channels that traverse separation wall (2), and as a consequence, concentrate in the first compartment (4). After the fluid fills the subsequent first and the second compartment it becomes quiescent, allowing optical examination.

FIG. 2 shows a separation wall having two different channels of different sizes (9) and (10). The channel labeled (9) is sized to allow only particles smaller than a certain size to pass and the channel labeled (10) is sized to allow only liquid to pass. It has been found through experimentation that these channels can be sized appropriately to exclude cell or particle sizes of interest.

FIG. 3 shows a separation wall (16) with a plurality of one type of separating channel (17) disposed laterally across its full width.

FIG. 4 shows another embodiment of the separating channels, with a plurality of a first channel (14) which allows cellular or particulate species to pass through it, while allowing a liquid portion devoid of this species to pass through a plurality of a second channel (15) disposed in an array alongside the first channel (14).

Figure 5:
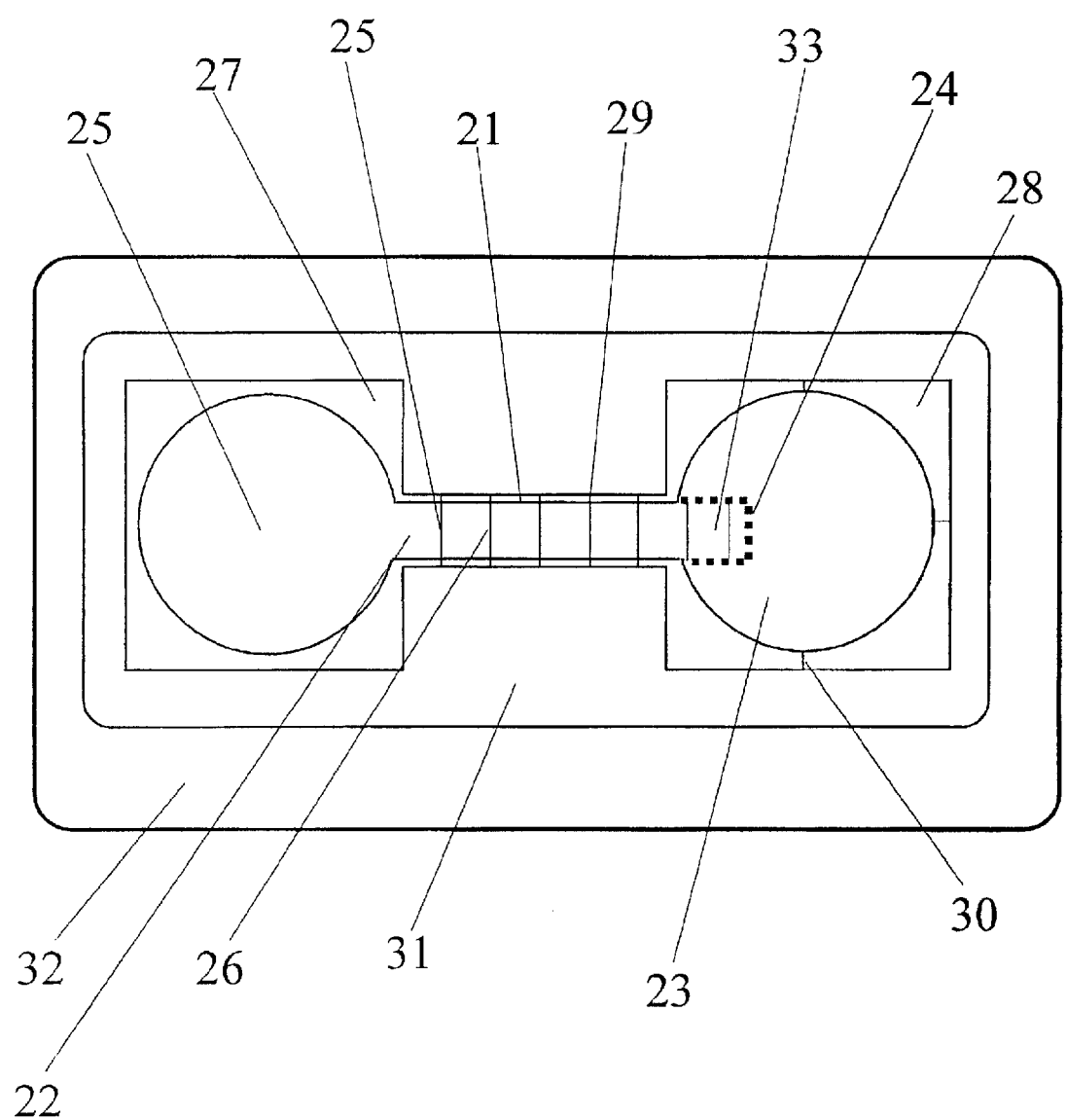
FIG. 5 is a schematic view of a particle separation chamber with increased analytical sensitivity.

In another embodiment of the present invention, which is depicted in FIG. 5, increased analytical sensitivity can be attained by enlarging the volume of the second compartment, allowing the sample portion in the first compartment to accumulate larger cells over an increased volume.

In the embodiment of FIG. 5, the separation chamber is surrounded by a wall (21) which is again used to carry an optically transparent lid (not shown) allowing for optical observation and to contain the liquid sample. The separation chamber is divided into two compartments (22) and (23) by a separation wall (24) which has the separation channels on top of it. Separation wall (24) is U-shaped in order to make it as long as possible. In operation, fluid fills the first compartment (22) through a sample entrance (25), which is surrounded by an extension (27) of wall (21), and moves into the first compartment (22) of the chamber. Upon proceeding, the liquid encounters a first notch (25) displaced laterally across the flow path. The notch creates a momentary barrier to progression of the advancing fluid meniscus until the meniscus has contacted the notch across the whole width of the chamber. Eventually the fluid wets into the notch, allowing the fluid to advance to the next notch (26) where the meniscus is again evened out. The fluid advance continues in this manner until it reaches separation wall (24). The fluid continues to advance through separation wall (24) and the separation channels to the second compartment (23) which is surrounded by wall extension (28). Wall (21) and wall extension (28) are equipped with air-venting channels (29) and (30), respectively. To allow for a free passage of air out of channels (29) and (30), walls (21), (27), and (28) are surrounded by a moat (31) in base plate (32). The lid is resting on walls (21), (27), and (28).

During the filling process, the particles of interest are prevented from passing through the separation channels that traverse separation wall (24), and as a consequence, concentrate in the first compartment in a U-shaped area (33) in front of separation wall (24). As mentioned above, compartment (23) behind separation wall (24) has an increased volume, which, in connection with the elongated U-shaped separation wall (24) allows one to process a larger sample volume, as compared to the embodiments shown in FIGS. 1, 2, 3, and 4. In other words, the embodiment of FIG. 5 is suitable to achieve reasonable particle concentrations for analysis in front of separation wall (24), even if the particle concentration in the incoming sample is rather low.

What is claimed is:

1. A method for obtaining a liquid sample having an increased cellular or particulate concentration for optical examination comprising:

(a) providing an apparatus comprising:

a separation chamber;

a wall surrounding said separation chamber;

a sample entrance;

venting channels;

a separation wall in said separation chamber, dividing said chamber into two compartments, said separation wall having at least one separation channel, whereby said at least one separation channel has the appropriate size and dimensions to allow undesired cellular or particulate species to pass through, while excluding larger desired cellular or particulate species from passing through; and a flow path in said separation chamber;

(b) depositing a liquid sample into the sample entrance of said apparatus;

(c) allowing the sample to flow into the separation chamber;

(d) allowing the sample to flow along the flow path in said separation chamber;

(e) allowing the sample to advance to the separation wall;

(f) allowing the sample to advance through the separation wall and the at least one separation channel;

(g) allowing the portion of the sample containing undesired cellular or particulate species to advance to the second compartment;

(h) allowing the sample to advance to the end of the separation chamber; and (i) obtaining in the first compartment the sample having an increased cellular or particulate concentration, which has been prevented from passing through said separation channel(s).

2. The method according to claim 1 wherein said liquid sample is blood.

3. The method according to claim 1 wherein said apparatus further comprises a lid portion.

4. The method according to claim 3 wherein said lid portion has at least one opening for sample delivery.

5. The method according to claim 1 wherein said separation wall has at least one first separation channel and at least one second separation channel.

6. The method according to claim 5 wherein said separation channels are of different sizes.

7. The method according to claim 5 wherein said first separation channel is about 3 to 10 $\mu$m deep by 5 to 50 $\mu$m wide.

8. The method according to claim 5 wherein said second separation channel is about 0.5 to 1.5 $\mu$m deep by 50 to 1000 $\mu$m wide.

9. The method according to claim 1 wherein said apparatus further comprises a plurality of notches in said separation chamber.

10. The method according to claim 1 wherein said apparatus further comprises a plurality of notches in said first compartment of said separation chamber.

11. The method according to claim 1 wherein said apparatus further comprises a plurality of notches in said second compartment of said separation chamber.

12. The method according to claim 1 wherein said apparatus further comprises a plurality of notches in said first compartment and second compartment of said separation chamber.

13. The method according to claim 1 wherein said separation wall has a plurality of separation channels of the same size.

14. The method according to claim 1 wherein said separation wall has a plurality of separation channels of different sizes.

15. The method according to claim 9, further comprising allowing the sample to flow past each notch in the separation chamber.

16. The method according to claim 10 further comprising, after step (d), allowing the sample to flow past each notch in the first compartment.

17. The method according to claim 11 further comprising, after step (g), allowing the sample to flow past each notch in the second compartment.

18. The method according to claim 12 further comprising, after step (d), allowing the sample to flow past each notch in the first compartment; and after step (g), allowing the sample to flow past each notch in the second compartment.

* * * * *